United States Patent [19]

Bunge et al.

[11] Patent Number: 4,530,835

[45] Date of Patent: Jul. 23, 1985

[54] CL-1577 ANTIBIOTIC COMPOUNDS AND THEIR PRODUCTION

[75] Inventors: Richard H. Bunge; James C. French; Timothy R. Hurley; Tim A. Smitka, all of Ann Arbor; Josefino B. Tunac, Troy, all of Mich.

[73] Assignee: Warner-Lambert Company, Morris Plains, N.J.

[21] Appl. No.: 512,088

[22] Filed: Jul. 8, 1983

[51] Int. Cl.$^3$ .................... A61R 35/74; C12P 1/06
[52] U.S. Cl. .................................. 424/117; 435/169
[58] Field of Search ..................... 424/117; 435/169

[56]  References Cited

FOREIGN PATENT DOCUMENTS 95154  11/1983  European Pat. Off. ............ 424/117

Primary Examiner—Jerome D. Goldberg
Attorney, Agent, or Firm—Jerry F. Janssen

[57] ABSTRACT

A purified isolate of an actinomycete identified as ATCC 39363 is capable of producing a complex of sulfur-containing antibiotic compounds having activity against transplanted tumors.

Antibiotic compounds CL-1577A and CL-1577B and their closely related congeners are produced by cultivating isolate ATCC 39363 under aerobic conditions in a culture medium containing assimilable sources of carbon and nitrogen until a substantial quantity of the CL-1577 complex is produced, and subsequently isolating the complex or one or more of the compounds.

The antibiotic compounds CL-1577A, CL-1577B, their congeners, and pharmaceutical compositions comprising these substances together with a suitable carrier are also disclosed.

5 Claims, 6 Drawing Figures

CL-1577 ANTIBIOTIC COMPOUNDS AND THEIR PRODUCTION

BACKGROUND OF THE INVENTION

The present invention relates to a complex of novel, sulfur-containing antibiotic compounds demonstrating activity against transplanted tumors designated CL-1577A and CL-1577B and their congeners, to pharmaceutically acceptable derivatives thereof, to a process for the production of said compounds, and to a purified isolate of an actinomycete capable of producing these compounds.

More particularly, the process of producing the CL-1577 complex of antibiotic compounds relates to an aerobic fermentation process using a purified isolate of an actinomycete ATCC 39363.

SUMMARY OF THE INVENTION

In accordance with one aspect of the present invention, there is provided a purified isolate of an actinomycete having the identifying characteristics of ATCC 39363 which is capable of producing the antibiotic complex CL-1577, particularly the compounds CL-1577A, CL-1577B and their congeners.

In another aspect of the invention, there is provided a process for producing CL-1577 complex, CL-1577A, CL-1577B, and their congeners by cultivating the actinomycete isolate identified as ATCC 39363 under aerobic conditions in a medium containing assimilable sources of carbon and nitrogen until a substantial quantity of the CL-1577 complex is produced, and subsequently isolating the complex, or CL-1577A and CL-1577B compounds.

In accordance with another aspect of the invention there are provided the antibiotic compounds CL-1577A, CL-1577B and their pharmaceutically acceptable derivatives, which compounds exhibit both antibiotic and antitumor properties.

In another aspect of the present invention, there are supported pharmaceutical compositions comprising at least one CL-1577A and CL-1577B compound, their pharmaceutically acceptable derivatives and, optionally, additional antibiotic compounds together with a pharmaceutically acceptable carrier.

BRIEF DESCRIPTION OF THE DRAWING

FIGS. 1a, 1b, and 1c are the ultraviolet, infrared, and 200 MHz proton magnetic resonance spectra, respectively, of the compound designated CL-1577A.

FIGS. 2a, 2b, and 2c are the ultraviolet, infrared, and 200 MHz proton magnetic resonance spectra, respectively, of the compound designated CL-1577B.

DETAILED DESCRIPTION

In accordance with the present invention, the CL-1577 complex of antibiotic compounds is produced by cultivating a selected isolate of actinomycete, ATCC 39363, under artificial conditions until a substantial quantity of CL-1577 complex (especially CL-1577A and CL-1577B) is formed, and subsequently isolating one or more of the compounds.

The actinomycete isolate suitable for the purpose of this invention was found in a soil sample collected in Tennessee, USA. This microorganism was isolated from the soil sample using a suitable agar plating medium, one containing salts such as potassium phosphate, potassium chloride, magnesium sulfate, and ferrous sulfate, and carbon sources such as glycerol and asparagine. To isolate the microorganism, the soil sample is pretreated with calcium carbonate before being plated onto the agar medium and, once plated, is incubated at a favorable temperature, particularly 33° C., to allow for the development of the soil microorganisms.

The CL-1577 complex producing organism that was isolated from the soil sample by the agar plating technique is an unidentified actinomycete and has been deposited with the American Type Culture Collection, Rockville, Md. 20852, where it is being maintained in their permanent culture collection as ATCC 39363. This organism, designated as culture WP-444, which produces CL-1577A, CL-1577B and their congeners, is also being maintained as a dormant culture in lyophile tubes, cryogenic vials, and in soil tubes in the Warner-Lambert/Parke-Davis Culture Collection, 2800 Plymouth Road, Ann Arbor, Mich. 48105.

The compounds CL-1577A, CL-1577B, and their closely related congeners, which demonstrate both antibiotic and antitumor properties, are produced by isolate ATCC 39363 during aerobic fermentation under controlled conditions. The fermentation medium consists of sources of carbon, nitrogen, minerals, and growth factors. Examples of carbon sources are glycerol and various simple sugars, such as glucose, mannose, fructose, xylose, ribose, or other carbohydrate-containing compounds such as dextrin, starch, cornmeal, and whey. The normal quantity of carbon source materials in the fermentation medium varies from about 0.1 to about 10 weight percent.

Nitrogen sources in the fermentation medium are organic, inorganic, or mixed organic-inorganic material. Examples of such materials are cottonseed meal, soybean meal, corn germ flour, corn steep liquor, distillers dried solubles, peanut meal, peptonized milk, and various ammonium salts.

The addition of minerals and growth factors are also helpful in the production of the CL-1577 complex of compounds. Examples of fermentation medium mineral additives include potassium chloride, sodium chloride, ferrous sulfate, calcium carbonate, cobaltous chloride, and zinc sulfate. Sources of growth factors include various yeast and milk products.

The preferred method for producing the CL-1577 complex of compounds is by submerged culture fermentation. According to this embodiment of the invention, the fermentation ingredients are prepared in solution or suspension and the mixture subsequently sterilized by autoclaving or steam heating. The pH of the aqueous medium is adjusted to preferably between about pH 4 and about pH 8 and the mixture cooled following sterilization to a temperature between about 16° C. to about 45° C. The cooled, sterile fermentation medium is inoculated with the organism and thereafter fermentation is carried out with aeration and agitation.

In the submerged culture method, fermentation is carried out in shake-flasks or in stationary tank fermentors. In shake-flasks, aeration is achieved by agitation of the flasks to bring about mixing of the medium with air. In stationary tank fermentors, agitation is provided by impellers which may take the form of disc turbines, vaned discs, open turbine or marine propellers. Aeration is accomplished by injecting air or oxygen into the agitated mixture.

Adequate production of the CL-1577 complex of compounds is normally achieved under these conditions after a period of about two to ten days.

In an alternative embodiment, the CL-1577 complex of compounds may also be produced by solid state fermentation of the microorganism.

The following examples are provided to enable one skilled in the art to practice the present invention and are merely illustrative thereof. They are not to be viewed as limiting the scope of the invention as defined by the appended claims.

FERMENTATIVE PRODUCTION OF CL-1577 COMPLEX

Example 1

The culture of Streptomyces sp. (ATCC 39363) of the present invention, following its isolation from the agar plate, was transferred to an agar slant employing CIM 23 medium and incubated at 28° C. for 7 to 14 days.

TABLE I

| Formulation of CIM 23 Medium | |
|---|---|
| Amidex corn starch | 1.0% |
| N—Z amine, type A | 0.2% |
| Beef Extract (Difco) | 0.1% |
| Yeast Extract (Difco) | 0.1% |
| Cobalt chloride pentahydrate | 0.002% |
| Agar | 2.0% |

Example 2

A portion of the microbial growth from the agar slant was used to inoculate an 18-mm×150-mm seed tube containing 5 ml of ARM 1550 seed medium. The inoculated seed was shaken at 33° C. for three days.

TABLE II

| Formulation of ARM 1550 Seed Medium | |
|---|---|
| Bacto-Yeast extract (Difco) | 0.5% |
| Glucose monohydrate | 0.1% |
| Soluble starch (Difco) | 2.4% |
| Bacto-tryptone (Difco) | 0.5% |
| Bacto-Beef extract (Difco) | 0.3% |
| Calcium carbonate | 0.2% |

Note:
pH is adjusted to 7.5 with NaOH prior to adding the calcium carbonate.

Example 3

A 1-ml portion of the microbial growth from the seed tube was transferred to a 300-ml baffled shake-flask containing 50 ml of SM-13 production medium.

TABLE III

| Formulation of SM-13 Production Medium | |
|---|---|
| Dextrin-Amidex B411 (American Maize) | 1.5% |
| Lactose (Mallinckrodt) | 1.0% |
| Pharmamedia (Traders) | 0.65% |
| Fish meal (Zapata Haynie) | 0.35% |
| Torula yeast (St. Regis) | 0.25% |

The inoculated flask contents were incubated at 33° C. for four days with shaking (170 rpm gyratory shaker, 5 cm throw.) After a five day period, the fermentation beer was tan in color, the mycelia was granular in appearance, and the pH of the beer was about 6.4.

The antitumor activity of this fermentation broth was assayed at a dilution of 1:100 versus L1210 mouse leukemia cells grown in tissue culture. The assay technique is fully described in Cancer Chemotherapy Reports, Part 3, Vol. 3, No. 2 (1972), Deran, Greenberg, MacDonald, Schumacher and Abbott. A broth which gave L1210 leukemia cell growth rates of 0 to 35%, compared with the growth of these cells under control conditions, was considered active, 0%, most active. The observed activities of the fermentation broth of Example 3 are given in Table IV.

TABLE IV

Antitumor Activity of Fermentation Broth from Example 3 (As Measured Against L1210 Mouse Leukemia Cells)

| | % L1210 Cell Growth | |
|---|---|---|
| Flask Number | Supernate | Freeze-Dried Ethanol Extract |
| I | — | 8 |
| II | 10 | 31 |

The crude fermentation broth was also tested for antibacterial activity against various organisms using the agar-disc method. The crude broth was found to be active against *Alcaligenes viscolactis, Bacillus subtilis, Micrococcus luteus, Branhamella catarrhalis,* and *Staphylococcus aureus.*

Example 4

A cryogenic vial containing approximately 1 ml of a suspension of the culture was used to inoculate 600 ml of SD-05 seed medium contained in a 2-liter baffled shake-flask. The inoculated flask contents were incubated for 76 hours at 33° C. on a gyratory shaker at 130 rpm.

TABLE V

| Formulation of SD-05 Seed Medium | |
|---|---|
| Amberex 1003 (Amber Laboratories) | 0.5% |
| Glucose monohydrate (Cerelose, Corn Products) | 0.1% |
| Dextrin-Amidex B 411 (American Maize) | 2.4% |
| N—Z Case (Humko Sheffield) | 0.5% |
| Spray-dried meat solubles (Daylin Labs) | 0.3% |
| Calcium carbonate | 0.2% |

After 76 hours, the contents of the seed flask were transferred aseptically to a 30-liter stainless steel fermentator containing 16 liters of SD-05 seed medium. The inoculated fermentor contents were incubated at 33° C. for 24 hours while being stirred at 300 rpm and sparged with air at a rate of 1 vol/vol/min.

Example 5

The microbial growth from Example 4 was used to inoculate 75 gallons (284 liters) of SD-05 seed medium contained in a 200-gallon (757-liter) stainless steel fermentor. The medium was sterilized by steam heating at 121° C. for 40 minutes. The fermentor and contents were cooled to 33° C. and then inoculated with about 16 liters of the broth from Example 4. The resulting mixture was incubated at 33° C. for about 20 hours with stirring at 155 rpm, and sparged with air at a rate of 0.75 vol/vol/min.

Example 6

The microbial growth from Example 5 was used to inoculate about 1300 gallons (4921 liters) of SM-121 medium contained in a 2000 gallon (7571 liter) stainless steel fermentor. The medium was sterilized prior to inoculation by heating with steam for 40 minutes at 121° C. After sterilization, the fermentor and contents were cooled to 33° C., inoculated, and incubated for five days with stirring at 125 rpm and air sparging at a rate of 0.75 vol/vol/min.

The SM-121 medium consisted of 1.75% by weight of a feed grade mixture composed of soybean meal, ground yellow corn, ground wheat, corn gluten meal, wheat middlings, dried milk products, animal fat preserved with BHA, ground beet pump, calcium carbonate, sucrose, dehydrated alfalfa meal, dicalcium phosphate, brewers' dried yeast, salt, vitamin $B_{12}$ supplement, riboflavin supplement, calcium pantothenate, niacin, choline chloride, menadione sodium bisulfite (source of vitamin K activity), folic acid, pyridoxine hydrochloride, thiamin, ascorbic acid, vitamin A supplement, D activated animal sterol (source of vitamin $D_3$), vitamin E supplement, iron carbonate, iron sulfate, calcium iodate, manganous oxide, copper oxide, cobalt carbonate, zinc oxide.

The production of CL-1577 complex was monitored throughout the fermentation cycle by in vitro assay against L1210 mouse leukemia cells and by antimicrobial activity against *Micrococcus luteus*. In addition, such fermentation parameters as pH and percent sedimentation were recorded throughout the fermentation cycle. The data are presented in Table VI.

trated in a vacuum evaporator to a volume of three liters. The oily residue which remained on the inside walls of the evaporator was dissolved in 5 liters of ethyl acetate. The 3 liter concentrate was thrice extracted with 1.5-liter portions of ethyl acetate and the four ethyl acetate solutions combined and dried over about 3 kg of anhydrous sodium sulfate. The drying agent was filtered off and washed with 3 liters of ethyl acetate. The filtrate and drying agent wash were combined and the resulting solution was passed through a chromatographic column (15-cm i.d.) containing 2.5 kg of 40 μm aminopropyl-silica gel (Analytichem International, Inc., Harbor City, CA) which had been prewashed with methanol and equilibrated with ethyl acetate.

The first 4 liters of eluate were found to contain no CL-1577 complex and were discarded. The material adsorbed on the chromatographic column was eluted with a total volume of 36.1 liters of ethyl acetate and the eluate was concentrated to a volume of about 600 ml. A small amount of insoluble material in the eluate was filtered off and the filtrate was treated with 5 liters of petroleum ether (bp 30°-60° C.) to precipitate 12.75 g of CL-1577 complex.

The solid was triturated with 300 ml of methanol and the insoluble material was removed by filtration. The

TABLE VI

| | | | | Observed Bioactivity | | | | | |
|---|---|---|---|---|---|---|---|---|---|
| | | | Inhibition of Growth of *Micrococcus luteus* Inhibition Zone Dia. | Percent Growth of L1210 Mouse Leukemia Cells at Given Dilution | | | | | |
| Fermentation Time (Hours) | pH | Percent Sedimentation (Growth) | (mm) | 1:500 | 1:2500 | 1:5000 | 1:10,000 | 1:30,000 | 1:100,000 |
| 0 | 6.65 | 0 | 0 | NA* | — | NA* | — | — | — |
| 24 | 8.10 | 10.0 | 0 | NA* | — | NA* | — | — | — |
| 46 | 7.40 | 29.3 | 17 | 5.1 | — | 13.9 | — | — | — |
| 75 | 7.30 | 25.4 | 21 | — | 2.3 | — | 7.6 | 15.7 | 29.2 |
| 96 | 7.90 | 20.0 | 22 | — | 2.8 | — | 5.8 | 12.1 | 17.1 |
| 116 | 8.20 | 25.4 | 22.5 | — | 1.6 | — | 4.7 | 11.2 | 30.4 |

*NA = Not active.

After 116 hours of fermentation, the 1140 gallons (4315 liters) of fermentation beer were harvested and the CL-1577 complex of compounds isolated as described below.

CHEMICAL ISOLATION OF CL-1577 COMPLEX

Example 7

The pH of the fermentation beer from Example 6 was adjusted to 6.2 and stirred for about two hours with 3000 liters of ethyl acetate. The mixture was treated with 68 kg of Celite 545 filter aid and then filtered through a 79-cm plate-and-frame filter press. The filtrate was allowed to stand and the lower aqueous layer which separated was removed and extracted with an additional 2070 liters of ethyl acetate. The organic solutions were combined and concentrated in vacuo to a final volume of 20 liters. Upon standing at 5° C. overnight, a lower layer of approximately 900 ml separated. This layer was found to contain only trace amounts of CL-1577 complex and was discarded.

The upper layer of approximately 19 liters was filtered through Celite 545 filter aid to remove insoluble materials and then washed with 2 liters of water. To the ethyl acetate solution were added with stirring, 15 liters of a 50:50 water-methanol mixture and then 45 liters of petroleum ether (bp 30°-60° C.). The resulting two-phase mixture was allowed to stand and the upper organic layer was removed and extracted a second time with 15 liters of a 50:50 water-methanol mixture. The aqueous methanol extracts were combined and concentrated filtrate was diluted with 130 ml of water and the trace of insoluble material was filtered off to produce a filtrate designated "filtrate A."

A 7-cm (i.d.) stainless steel chromatographic column was dry-packed with 1.9 kg of 40 μg $C_{18}$-silica gel (Analytichem International, Inc., Harbor City, CA) and then sequentially washed with methanol, 50:50 methanol-water, 20:10:70 methanol-acetonitrile-0.05M sodium acetate buffer (pH 5.1), and finally 75:25 methanol-water. Filtrate A was charged to this column and eluted with 17 liters of 75:25 methanol-water followed by 1.3 liters of methanol. CL-1577A and CL-1577B were collected in the final 1.3 liter methanol eluate fraction.

The methanol fraction was concentrated in vacuo to an oily residue which was taken up in 30 ml of ethyl acetate. The ethyl acetate solution was treated with 300 ml of petroleum ether (bp 30°-60° C.) to precipitate 3.4 g of a mixture containing CL-1577A and CL-1577B.

CHEMICAL ISOLATION OF CL-1577A

Example 8

The product (3.4 gm) of CL-1577A, and CL-1577B from example 7 was dissolved in 40 ml of methanol. The resulting solution was diluted with 10 ml of water and chromatographed on the 7 cm (i.d.) $C_{18}$ silica gel column described above using 80:20 methanol-0.05M ammonium acetate buffer (pH 6.8) as the eluent. The flow rate was adjusted to about 200 ml/min and the eluate monitored by measuring its ultraviolet absorption at 254 nm.

The first major UV-absorbing fraction was eluted at a k' value of 2.5 (1.8 liters) and was designated "solution A." (The value of k' is given by the expression $k'=(Ve-Vo)/Vo$ where Vo is the void volume, 2.0 liters, and Ve is the volume eluted at maximum ultraviolet absorption.)

Solution A was concentrated in vacuo to a volume of 100 ml and the concentrate extracted with two successive 40-ml portions of chloroform. The chloroform extracts were combined, dried over anhydrous sodium sulfate, and concentrated to a volume of 25 ml. Addition of 300 ml of petroleum ether (bp 30°-60° C.) caused the precipitation of a solid product designated CL-1577A.

This material was dissolved in 3 ml of 65:35 methanol-water and rechromatographed using a Prep 500 LC Apparatus (Waters Instruments, Inc., Milford, MA) fitted with a PrepPAK-500 ™ C-18 column employing 55:20:25 methanol-acetonitrile-0.05M ammonium acetate buffer (pH 6.8) as the eluent.

The eluate was monitored by measuring its refractive index. The fraction containing CL-1577A was eluted at k'=4.5. This fraction was concentrated to 85 ml and extracted with three 30 ml portions of chloroform which were combined and dried over anhydrous sodium sulfate. Addition of 250 ml of n-haxane to the dried and filtered solution precipitated 0.242 g of CL-1577A which was found to be 95% pure by high pressure liquid chromatographic analysis.

Figure 1A:
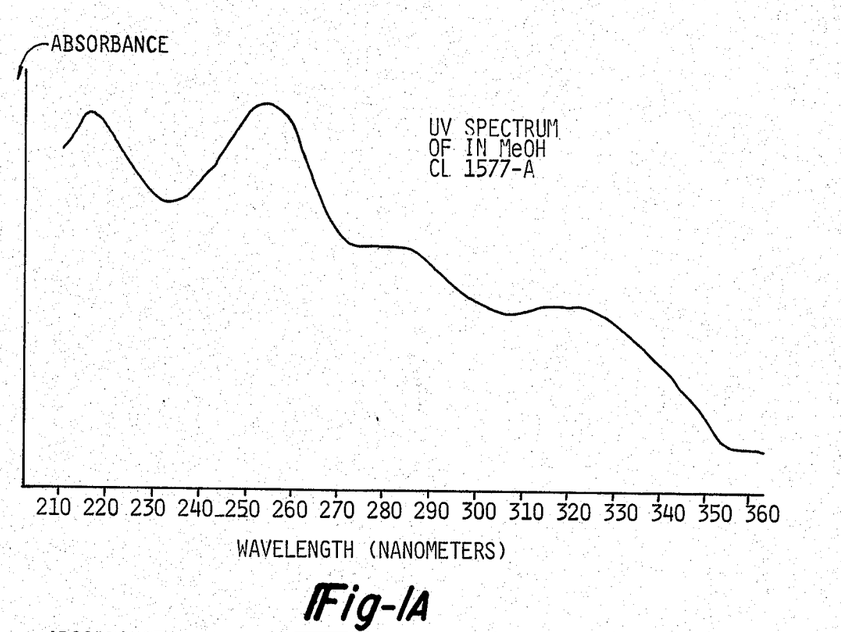
Figure 1B:
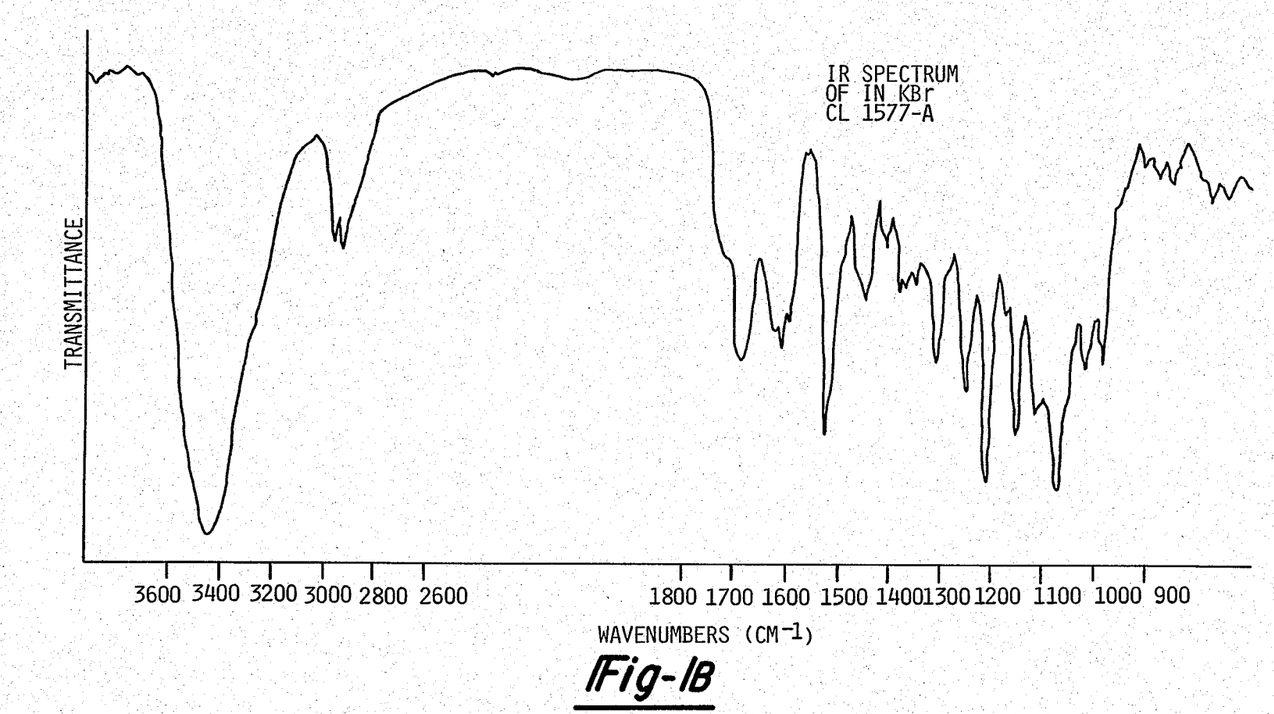
Figure 1C:
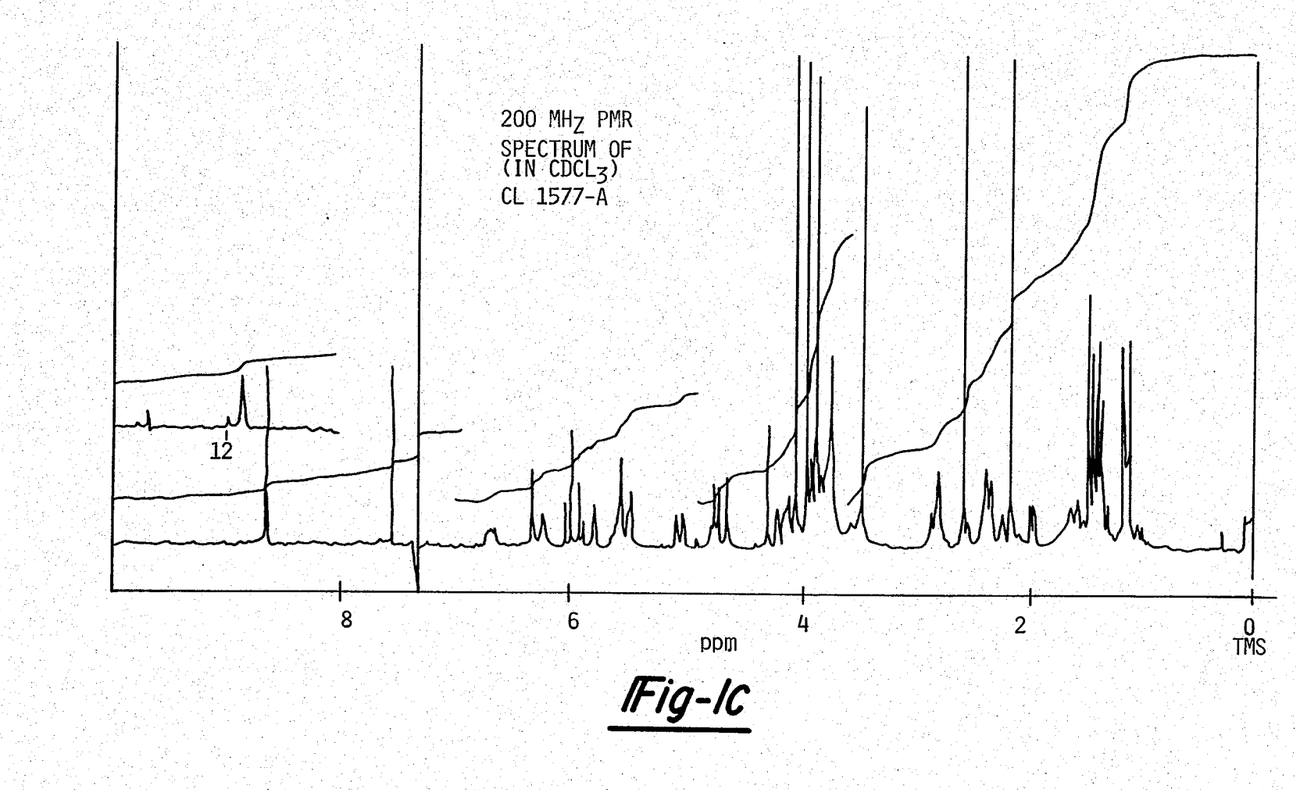

The chemical and physical properties of CL-1577A appear in Table VII and the ultraviolet, infrared, and 200 MHz proton magnetic resonance spectra of the compound appear as FIGS. 1a, 1b, and 1c, respectively.

CHEMICAL ISOLATION OF CL-1577B

Example 9

The second major ultraviolet-absorbing fraction eluted from the chromatographic column described in Example 8 was eluted at a k' of 3.5 (2.0 liters) and was designated "solution B."

Solution B was concentrated in vacuo and the concentrate was extracted with two successive 40 ml portions of chloroform. The chloroform extracts were combined, dried over anhydrous sodium sulfate, and filtered. The dried solution was concentrated to 25 ml and upon the addition of 300 ml of petroleum ether (bp 30°-60° C.), 0.456 g of CL-1577B precipitated.

A portion (0.43 g) of this material was dissolved in 3 ml of 65:35 methanol-water and chromatographed on the column described in Example 8 employing 55:20:25 methanol-acetonitrile-0.05M ammonium acetate buffer (pH 6.8) as the eluent. The eluate was monitored by measuring its refractive index. The CL-1577B compound was eluted at k'=7.5 in a 1.85 liter fraction. This solution was concentrated to 100 ml and extracted with three 35 ml portions of chloroform. The chloroform extracts were combined, dried, and concentrated to 20 ml. Addition of 300 ml of cyclohexane precipitated 0.30 g of CL-1577B which was found to be 95% pure by high liquid chromatographic analysis.

Figure 2A:
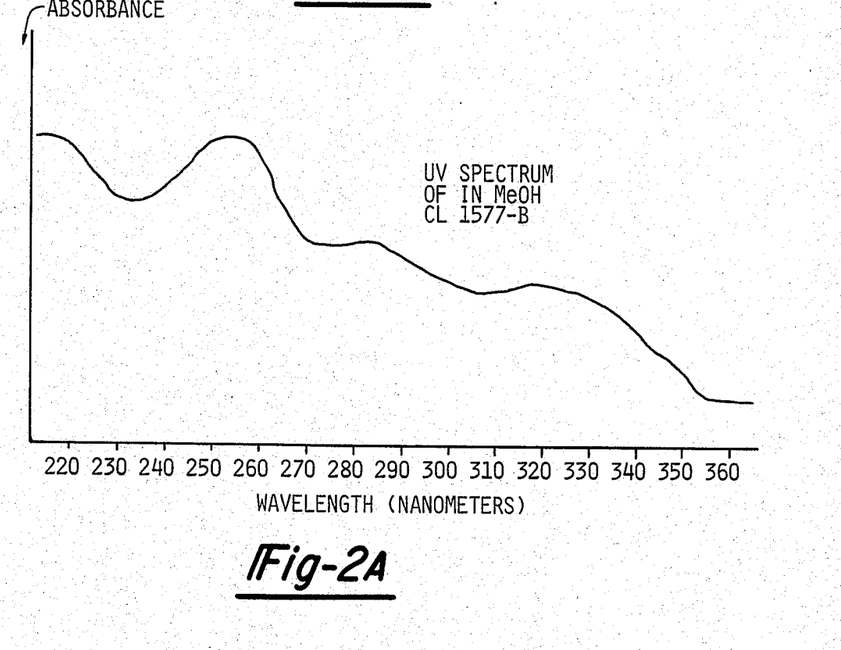
Figure 2B:
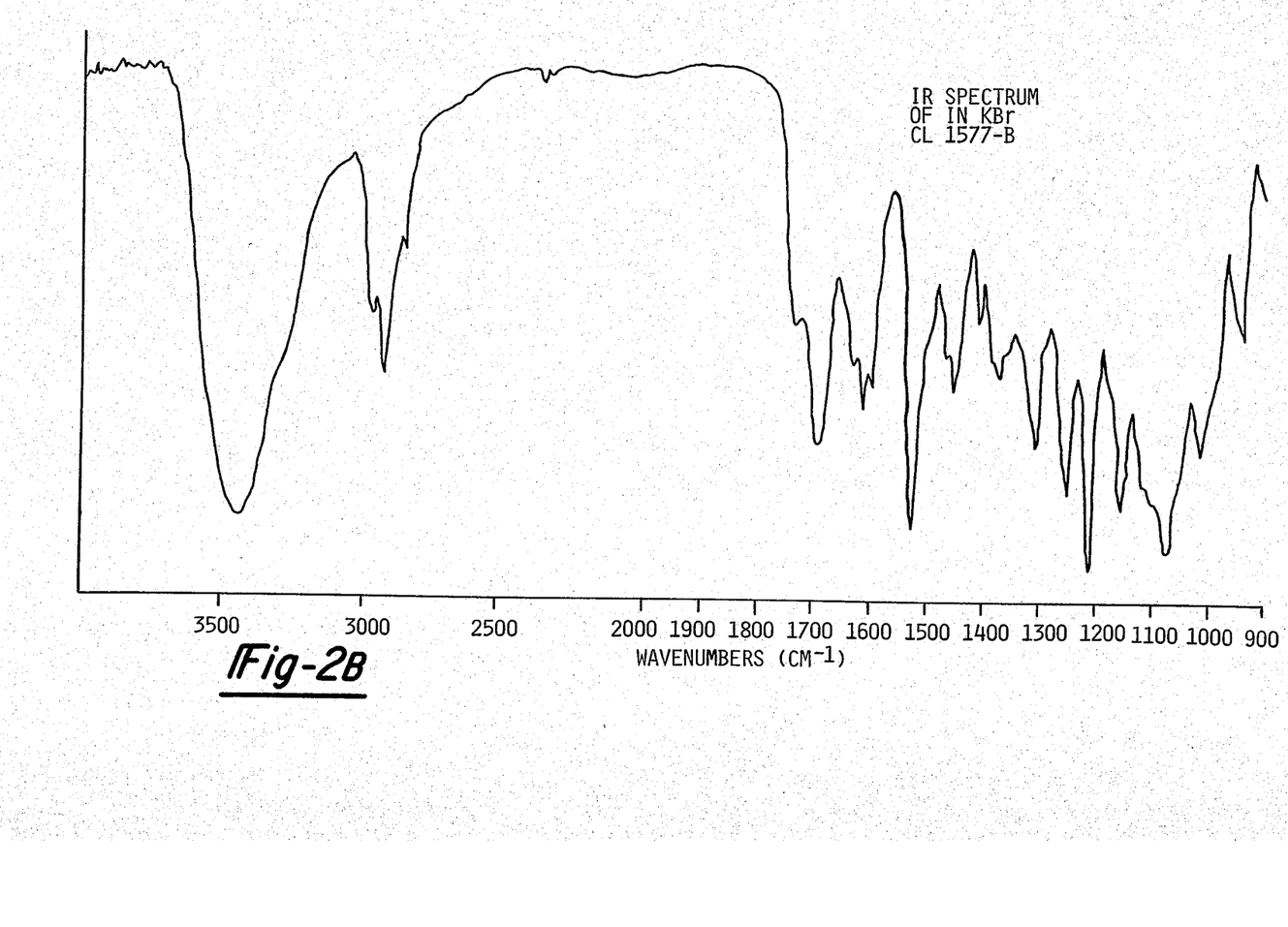
Figure 2C:
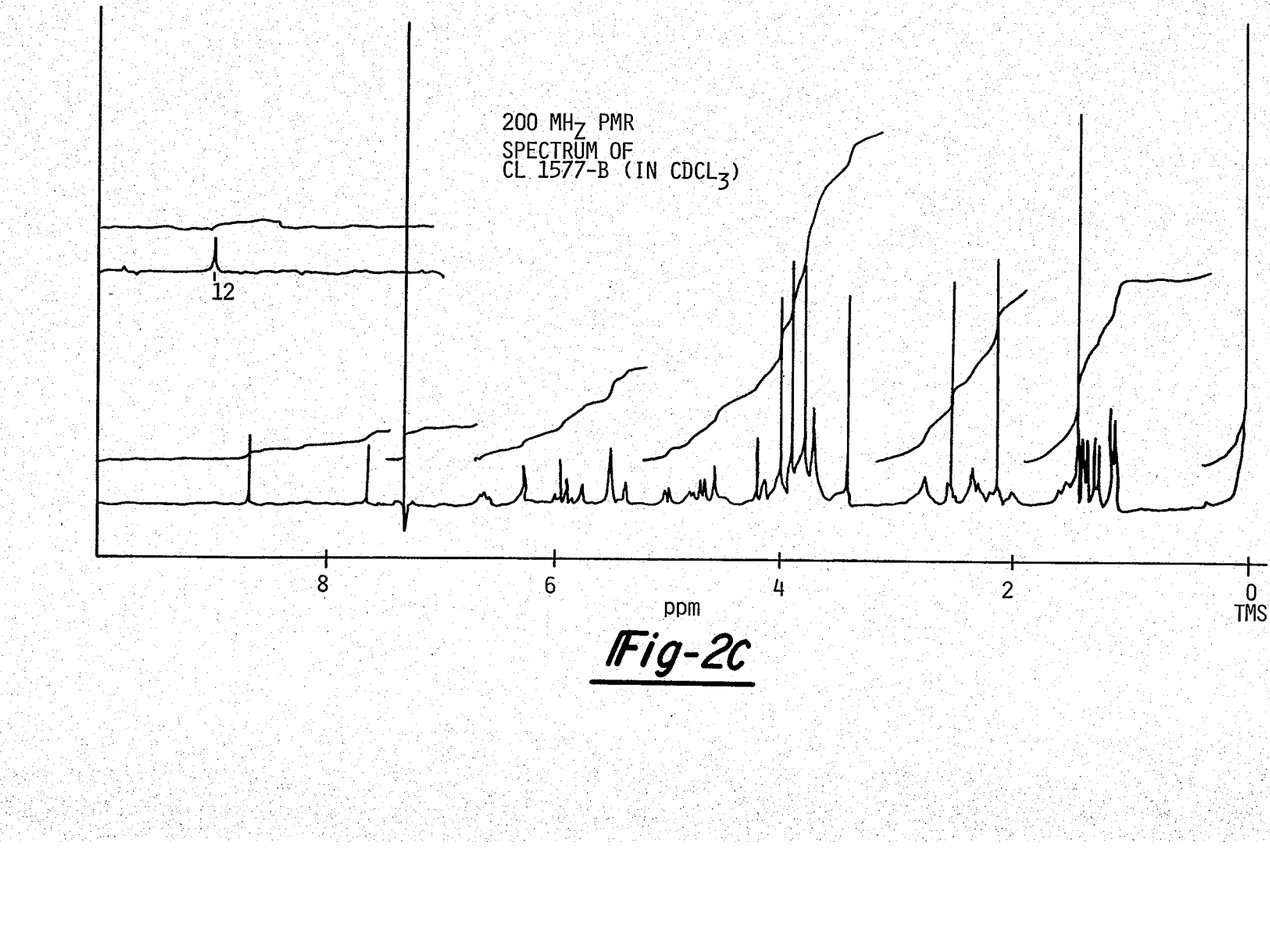

The chemical and physical properties of CL-1577B appear in Table VII and the ultraviolet, infrared and 200 MHz proton magnetic resonance spectra of the compound appear as FIGS. 2a, 2b, and 2c, respectively.

TABLE VII

| | Physical Properties of CL-1577A and CL-1577B | |
|---|---|---|
| Property | CL-1577A | CL-1577B |
| Ultraviolet absorption spectrum in methanol | λmax = 215 nm, a = 27.4<br>λmax = 252 nm, a = 28.2<br>λmax = 282 nm, a = 16.7<br>λmax = 318 nm, a = 11.6 | λmax = 215 nm, a = 26.8<br>λmax = 252 nm, a = 26.5<br>λmax = 282 nm, a = 16.1<br>λmax = 325 nm, a = 11.9 |
| Infrared absorption spectrum (KBr pellet; values given in reciprocal centimeters) | Principal absorption peaks at 3450, 2970, 2930, 1690, 1630, 1610, 1600, 1525, 1465, 1450, 1410, 1370, 1310, 1250, 1210, 1155, 1075, 1020, 990, 905, 880, 855, 795, and 750. | Principal absorption peaks at 3450, 2970, 2930, 1690, 1630, 1610, 1600, 1525, 1465, 1450, 1410, 1370, 1310, 1250, 1210, 1155, 1075, 1020, 945, 905, 880, 855, 795, 780, and 750. |
| 200 MHz Proton magnetic resonance spectrum in CDCl$_3$ (values given in ppm relative to tetramethylsilane; s = singlet, d = doublet, dd = doublet of doublets, t = triplet, q = quartet, m = multiplet) | 1.11 (d), 1.3 (d), 1.35 (d), 1.41 (d), 1.56 (m), 1.95 (d), 2.12 (m), 2.13 (s), 2.22 (m), 2.30(m), 2.52 (dd), 2.53 (s), 2.75 (m), 3.42 (s), 3.4–4.2 (m), 3.81 (s), 3.89 (s), 3.98 (s), 4.21 (s), 4.57 (d), 4.67 (m), 4.97 (d), 5.40 (m), 5.49 (d), 5.50 (m), 5.70 (d), 5.82 (d), 6.00 (d), 6.15 (broad s), 6.26 (s), 6.60 (dd), 7.49 (s), 8.60 (s), 11.71 (s) | 1.11 (d), 1.12 (d), 1.24 (d), 1.35 (d), 1.41 (s), 1.43 (s), 1.46 (m), 2.00 (m), 2.13 (s), 2.14 (m), 2.31 (m), 2.52 (s), 2.53 (m), 2.75 (m), 3.42 (s), 3.4–4.2 (m), 3.79 (s), 3.89 (s), 3.99 (s), 4.19 (s), 4.49 (m), 4.56 (d), 4.66 (d), 4.77 (m), 4.97 (m), 5.35 (broad s), 5.47 (m), 5.72 (d), 5.83 (d), 5.93 (d), 6.21 (m), 6.24 (s), 6.59 (dd), 7.61 (s), 8.64 (s), 11.58 (s). |
| Optical rotation | $[\alpha]_D = -198°$ (c 1.25, CHCl$_3$) | $[\alpha]_D = -189°$ (c 0.63, CHCl$_3$) |
| Melting point | 185°-195° C. with prior browning beginning at about 140° C. | 170°-195° with prior browning beginning at about 140° C. |
| Elemental analysis | 53.26% C; 6.04% H; 3.82% N; 8.98% S | 54.81% C; 6.33% H; 3.86% N; 8.96% S |
| Retention volume, HPLC (μBondpak ™ C$_{18}$ silica gel, 3.9 mm i.d. × 30 cm; eluent 55:20:25 methanol-acetonitrile-0.05M ammonium acetate buffer (pH 6.8)) | 12.02 ml | 26.26 ml |
| R$_f$ Value (Thin-layer chromatography; solvent: 9:1 methanol-0.1 M ammonium acetate buffer (pH 6.8); C$_{18}$ silica gel, 200 μm thickness; Whatman KC$_{18}$F ™ reversed phase TLC) | 0.5 | 0.43 |
| Molecular weight (FAB mass | 1248 | — |

TABLE VII-continued

| | Physical Properties of CL-1577A and CL-1577B | |
|---|---|---|
| Property | CL-1577A | CL-1577B |
| spectrometry | | |

BIOLOGICAL ACTIVITY OF CL-1577A AND CL-1577B

Example 10

The antimicrobial activity of CL-1577A and CL-1577B were evaluated by saturating 12.7 mm paper discs with a 500 μg/ml solution of either CL-1577A or CL-1577B, placing each saturated paper disc on a bioassay tray containing an agar medium seeded with a particular organism, incubating for 16 hours at 37° C. and measuring the diameter of the resulting growth inhibition zone, if any. The data for these tests appear in Table VIII.

TABLE VIII

Antimicrobial Activity of CL-1577A and CL-1577B

| Microorganism | Culture Number* | Medium | Growth Inhibition Zone Diameter (mm) CL-1577A | CL-1577B |
|---|---|---|---|---|
| Agrobacterium tumefaciens | PD 05037 | Mycin | 23 | 23 |
| Alcaligenes viscolactis | ATCC 21698 | TSA | 34 | 31 |
| Bacillus subtillis | PD 04555 | Mycin | 28 | 27 |
| Bacillus subtillis | PD 04555 | AM-21 | 32 | 33 |
| Bacillus subtillis | PD 04555 | AM-22 | 34 | 28 |
| Bacillus subtillis | PD H17 | AM-19 | 21 | 25 |
| Bacillus subtillis | PD M45 | AM-19 | 30 | 30 |
| Escherichia coli | PD 04524 | AM-18 | 17 | 20 |
| Escherichia coli | ATCC 25947 | AM-18 | 17 | 17 |
| Escherichia coli | PD 04863 | AM-23 | 23 | 22 |
| Escherichia coli | PD 04863 | AM-24 | 22 | 22 |
| Micrococcus luteus | PD 05064 | PAS | 30 | 29 |
| Penicillium avellaneum | PD M2988 | H & B | 31 | 24 |
| Streptococcus faecalis | PD 05045 | AM-9 | 27 | 26 |
| Streptococcus faecalis | PD 05045 | AM-10 | 24 | 24 |
| Streptococcus faecalis | PD 05045 | TSA | 18 | 17 |
| Streptococcus faecalis | PD 05045 | AM-11 | 26 | 26 |
| Streptococcus faecalis | PD 05045 | AM-12 | 25 | 24 |
| Streptococcus faecalis | PD 05045 | AM-13 | 25 | 22 |
| Streptococcus faecalis | PD 05045 | AM-14 | 23 | 21 |
| Turalopis albida | PD M1390 | 102 | 17 | 17 |

*ATCC = American Type Culture Collection, Rockville, Maryland 20852
PD = Warner-Lambert/Parke-Davis Culture Collection, 2800 Plymouth Road, Ann Arbor, Michigan 48105

Example 11

The antitumor activities of CL-1577A and CL-1577B against B16 melanocarcinoma in mice were evaluated using the test described in *Cancer Chemotherapy Reports*, Part 3, Vol. 3, 1–87, 1972. The data from these tests appear in Table IX. In each case, the mice were infected intraperitoneally on Day 0 and then given the indicated doses of CL-1577A or CL-1577B on Days 1, 5, and 9 of the test. The data are presented in terms of T/C values where:

$$T/C = \frac{\text{median survival time of treated mice}}{\text{median survival time of control mice}}$$

TABLE IX

In Vivo Antitumor Activity of CL-1577A and CL-1577B
(As Measured Against B16 Melanocarcinoma in Mice)

| | T/C (× 100) | |
|---|---|---|
| Dose (μg/kg of body weight) | CL-1577A | CL-1577B |
| 10 | Toxic | 206 |
| 5 | 196 | 160 |
| 2.5 | 201 | 172 |

TABLE IX-continued

In Vivo Antitumor Activity of CL-1577A and CL-1577B
(As Measured Against B16 Melanocarcinoma in Mice)

| | T/C (× 100) | |
|---|---|---|
| Dose (μg/kg of body weight) | CL-1577A | CL-1577B |
| 1.25 | 198 | 144 |

Example 12

The antitumor activities of CL-1577A and CL-1577B against P388 lymphocytic leukemia in mice were evaluated using the test described in *Cancer Chemotherapy Reports*, Part 3, Vol. 3, 1–87, 1972. The data from these tests appear in Table X. The mice were infected intraperitoneally on Day 0 and then given the indicated doses of CL-1577A or CL-1577B on Days 1, 5, and 9 of the test.

TABLE X

In Vivo Antitumor Activity of CL-1577A and CL-1577B
(As Measured Against P388 Lymphocytic Leukemia in Mice)

| | T/C (× 100) | |
|---|---|---|
| Dose (μg/kg of body weight) | CL-1577A | CL-1577B |
| 16 | Toxic | — |
| 10 | — | Toxic |
| 8 | 163 | — |
| 5 | — | 160 |
| 4 | 192 | — |
| 2.5 | — | 172 |
| 1.3 | — | 144 |

The antibiotic compounds CL-1577A and CL-1577B and their congeners can be used for their anti-microbial and antitumor activity in the form of pharmaceutical compositions in combination with a compatible pharmaceutically acceptable carrier. These compositions may also contain other antimicrobial agents. The compositions may be made up in any pharmaceutically appropriate form for the desired route of administration. Examples of such forms include solid forms for oral administration as tablets, capsules, pills, powders and granules, liquid forms for topical or oral administration as solutions, suspensions, syrups, and elixirs, and forms suitable for parenteral administration such as sterile solutions, suspensions, or emulsions.

For use as antimicrobial agents, the compositions are administered so that the concentration of the active ingredient or ingredients of the composition exceeds that required for the minimal inhibition of the particular microorganism sought to be controlled.

We claim:

1. A complex of sulfur-containing antibiotic compounds designated CL-1577A or CL-1577B,; compound CL-1577A characterized by:
    (a) a molecular weight (FAB mass spectrometry) of 1248 a.m.u.;
    (b) an ultraviolet absorption spectrum in methanol solution exhibiting absorption maxima at 215 nm (a=27.4), 252 nm (a=28.2), 282 nm (a=16.7), and 318 nm (a=11.6);
    (c) an infrared absorption spectrum (potassium bromide pellet) exhibiting principal absorption peaks at 3450, 2970, 2930, 1690, 1630, 1610, 1600, 1525, 1465, 1450, 1410, 1370, 1310, 1250, 1210, 1155, 1075, 1020, 990, 905, 880, 855, 795, 780, and 750 reciprocal centimeters;
    (d) a 200 MHz proton magnetic resonance spectrum (CDCl$_3$) exhibiting signals at 1.11 (doublet), 1.33 (doublet), 1.35 (doublet), 1.41 (doublet), 1.56 (multiplet), 1.95 (doublet), 2.12 (multiplet), 2.13 (singlet), 2.22 (multiplet), 2.30 (multiplet), 2.52 (doublet of doublets), 2.53 (singlet), 2.75 (multiplet), 3.42 (singlet), 3.4–4.2 (multiplet), 3.81 (singlet), 3.89 (singlet), 3.98 (singlet), 4.21 (singlet), 4.57 (doublet), 4.67 (multiplet), 4.97 (doublet), 5.40 (multiplet), 5.49 (doublet), 5.50 (multiplet), 5.70 (doublet), 5.82 (doublet), 6.00 (doublet), 6.15 (broad singlet), 6.26 (singlet), 6.60 (doublet of doublets), 7.49 (singlet), 8.60 (singlet), and 11.71 (singlet) parts per million downfield from tetramethylsilane;
    (e) an optical rotation $[\alpha]_D = -198°$ (c 1.25, CHCl$_3$); and
    (f) the elemental analysis, 53.26% C, 6.04% H, 3.82% N, and 8.98% S;

compound CL-1577B characterized by:
    (a) an ultraviolet absorption spectrum in methanol solution exhibiting absorption maxima at 215 nm (a=26.8), 252 nm (a=26.5), 282 nm (a=16.1), and 325 nm (a=11.9);
    (b) an infrared absorption spectrum (potassium bromide pellet) exhibiting principal absorption peaks at 3450, 2970, 2930, 1690, 1630, 1610, 1600, 1525, 1465, 1450, 1410, 1370, 1310, 1250, 1210, 1155, 1075, 1020, 945, 905, 880, 855, 795, 780, and 750 reciprocal centimeters;
    (c) a 200 MHz proton magnetic resonance spectrum (CDCl$_3$) exhibiting signals at 1.11 (doublet), 1.12 (doublet), 1.24 (doublet), 1.35 (doublet), 1.41 (doublet), 1.43 (singlet), 1.46 (multiplet), 2.00 (multiplet), 2.13 (singlet), 2.14 (multiplet), 2.31 (multiplet), 2.52 (singlet), 2.53 (multiplet), 2.75 (multiplet), 3.42 (singlet), 3.4–4.2 (multiplet), 3.79 (singlet), 3.89 (singlet), 3.99 (singlet), 4.19 (singlet), 4.49 (multiplet), 4.56 (doublet), 4.66 (doublet), 4.77 (multiplet), 4.97 (doublet), 5.35 (broad singlet), 5.47 (multiplet), 5.72 (doublet), 5.83 (doublet), 5.93 (doublet), 6.21 (multiplet), 6.24 (singlet), 6.59 (doublet of doublets), 7.61 (singlet), 8.64 (singlet), and 11.58 (singlet) parts per million downfield from tetramethylsilane; and
    (d) an optical rotation $[\alpha]_D = -189°$ (c 0.63, CHCl$_3$); and
    (e) the elemental analysis, 54.81% C, 6.33% H, 3.86% N, 8.96% S.

2. Compound CL-1577A as defined by claim 1.

3. Compound CL-1577B as defined by claim 1.

4. A pharmaceutical composition comprising an antibacterially effective amount of a compound selected from the group consisting of CL-1577A and CL-1577B, said compounds characterized as in claim 1, together with a pharmaceutically acceptable carrier.

5. A process for the production of CL-1577A or CL-1577B compound as defined in claim 1, which comprises cultivating a strain of Streptomyces sp., ATCC 39363, under aerobic conditions in a culture medium containing assimilable sources of carbon and nitrogen until a substantial amount of CL-1577A or CL-1577B is produced and subsequently isolating said CL-1577A or CL-1577B compound.

* * * * *